United States Patent [19]

Flanagan et al.

[11] 4,141,910

[45] Feb. 27, 1979

[54] AZIDO COMPOUNDS

[75] Inventors: Joseph E. Flanagan, Woodland Hills; Milton B. Frankel, Tarzana; Edward F. Witucki, Van Nuys, all of Calif.

[73] Assignee: Rockwell International Corporation, El Segundo, Calif.

[21] Appl. No.: 824,376

[22] Filed: Aug. 15, 1977

Related U.S. Application Data

[63] Continuation-in-part of Ser. No. 768,292, Feb. 14, 1977, abandoned.

[51] Int. Cl.$^2$ .......................................... C07C 117/00
[52] U.S. Cl. ...................................... 260/349; 149/88
[58] Field of Search .......................... 260/349; 149/88

[56] References Cited

U.S. PATENT DOCUMENTS

| | | | |
|---|---|---|---|
| 2,769,819 | 11/1956 | Sommers et al. | 260/349 |
| 3,122,570 | 2/1964 | Stansbury et al. | 260/349 |
| 3,405,144 | 10/1968 | Brownlee | 260/349 |
| 3,471,523 | 10/1969 | Harvey | 260/349 |
| 3,770,778 | 11/1973 | Trahanovsky et al. | 260/349 |
| 3,873,579 | 3/1975 | Rosher | 149/88 X |
| 3,883,377 | 5/1975 | Wright | 149/88 X |
| 4,020,176 | 4/1977 | Greenwald | 260/349 |

*Primary Examiner*—Leland A. Sebastian
*Attorney, Agent, or Firm*—L. Lee Humphries; Robert M. Sperry

[57] ABSTRACT

Organic azide compounds containing other energetic moieties such as fluorodinitro, trinitromethyl, nitramino, and gem-difluoroamino.

3 Claims, No Drawings

AZIDO COMPOUNDS

The invention herein described was made in the course of or under a contract or subcontract thereunder, (or grant) with the U.S. Air Force.

This invention is a Continuation-in-Part of U.S. Ser. No. 768,292 filed Feb. 14, 1977, and now abandoned.

BACKGROUND OF THE INVENTION

1. Field of Invention

This invention relates to compositions of matter and is particularly directed to organic azide compounds which contain other energetic chemical groups.

2. Description of the Prior Art

The development of advanced solid propellants, gun propellants and explosives requires the use of energetic, stable ingredients, including the oxidizer, binder and plasticizer. These ingredients must have a favorable preferably positive heat of formation and be oxygen-rich in order for a high performance to be met. Unfortunately, such compounds are not readily available. Moreover, these ingredients must have thermal and shock stability in order to permit safe storage and handling.

These disadvantages of the prior art are overcome with the present invention and new compositions of matter are proposed which are readily available and which are highly advantageous when formulated into propellant or explosive compositions.

BRIEF SUMMARY AND OBJECTS OF THE INVENTION

The advantages of the present invention are preferably attained by providing organic azide compounds which contain additional energetic chemical groups. It has been found that these azide compounds yield highly favorable heats of formation. For example, the heat of formation of ethanol is $-66.3$ kcal/mole, while 2-azido-ethanol has a heat of formation of $+22.5$ kcal/mole. Thus, the contribution of the azide moiety is approximately 85 kcal. For further comparison, the heat of formation of $[FC(NO_2)_2CH_2O]_2CH_2$ (FEFO) is $-165$ kcal/mole and the heat of formation of cyclotetramethylene tetranitramine (HMX) is $+5$ kcal/mole. Consequently, these axide compounds are useful as energetic plasticizers and, when combined with nitramino atoms, as oxidizers for solid propellants, gun propellants and explosive.

Accordingly, it is an object of the present invention to provide new compositions of matter.

Another object of the present invention is to provide new compositions of matter having high heats of formation.

An additional object of the present invention is to provide new compositions of matter having high heats of formation which have thermal and shock stability.

A further object of the present invention is to provide new compositions of matter having high heats of formation which can be employed as plasticizers or oxidizers in formulating solid propellants, gun propellants or explosives.

A specific object of the present invention is to provide new compositions of matter consisting of organic azide compounds which contain other energetic chemical groups in addition to the azido group.

These and other objects and features of the present invention will be apparent from the following detailed description.

DETAILED DESCRIPTION OF THE INVENTION

In the forms of the present invention chosen for purposes of illustration, the present invention teaches the preparation of organic azide compounds which contain other energetic chemical groups in addition to the azido group. Among the azide compounds which are useful for this purpose are azido-nitro compounds, including

I Ethers

A. $FC(NO_2)_2CH_2OCH_2OCH(CH_2N_3)_2$
B. $FC(NO_2)_2CH_2OCH_2N_3$

II Esters

A. $FC(NO_2)_2CH_2CH_2CO_2CH(CH_2N_3)_2$
B. $NO_2C(NO_2)_2CH_2CH_2CO_2CH(CH_2N_3)_2$

III Nitramines

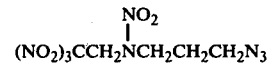

and azido-difluoramino compounds, such as

IV Alkanes

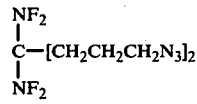

EXAMPLE I

Preparation of 1,3-Diazido-2-Propyl Fluorodinitroethyl Formal

A mixture of 10.1g (0.05m) of the chloromethyl ether of fluorodinitroethanol, 7.1g (0.05m) of 1,3-diazido-2-propanol, and 8 drops of stannic chloride was heated at 70° C. for 24 hours. The solution was dissolved in methylene chloride, washed with 1% sodium hydroxide solution, water, dried and concentrated to give 7g of yellow liquid. The product was purified by dissolving in a carbon tetrachloride/methylene chloride solution and passing through a basic alumina column. Concentration of the solution gave a light yellow liquid, $n_D^{25} = 1.4798$.

| Elemental Analysis: | C | H | N |
|---|---|---|---|
| Calculated for $C_6H_8FN_8O_6$: | 23.38 | 2.92 | 36.36 |
| Found: | 23.43 | 2.97 | 37.01 |

EXAMPLE II

Azidomethyl Fluorodinitroethyl Ether

To an aqueous solution of 6.5g (0.1m) of sodium azide in 25 ml water was added at ambient temperature a solution of 10.1g (0.05m) of the chloromethyl ether of fluorodinitroethanol in 25ml acetone. The solution was stirred overnight at ambient temperature, and heated 2 hours at 50° C. The solution was cooled, taken up in methylene chloride, washed with water, dried, and concentrated to give 9.9g (96%) of light yellow liquid, $n_D^{27} = 1.4478$, $d^{25} = 1.4707$.

| Elemental Analysis: | C | H |
| --- | --- | --- |
| Calculated for $C_3H_4FN_5O_5$: | 17.22 | 1.91 |
| Found: | 18.03 | 2.15 |

EXAMPLE III

Preparation of 1,7-Dichloro-4,4-difluoraminoheptane

To a solution of 25 ml of difluorosulfamic acid and 20 ml of methylene chloride was added dropwise in 25 minutes a solution of 1.85g (0.01 mole) of 1,7-dichloro-4-heptanone in 20 ml of methylene chloride. The temperature rose from 16 to 28° C. The reaction mixture was stirred for an additional two hours at ambient temperature. The methylene chloride layer was separated, washed with water, sodium bicarbonate solution, water, dried over magnesium sulfate, and concentrated to give 2.1g (77.7%) of colorless liquid, $n_D^{23} = 1.4456$.

| Elemental Analysis: | C | H | N |
| --- | --- | --- | --- |
| Calculated for $C_7H_{12}Cl_2F_4N_2$: | 31.00 | 4.43 | 10.33 |
| Found: | 30.99 | 4.81 | 9.84 |

EXAMPLE IV

Preparation of 1,7-Diazido-4,4-difluoraminoheptane

A mixture of 2.1g (0.0077 mole) of 1,7-dichloro-4,4-difluoraminoheptane, 2.0g (0.031 mole) of sodium azide, and 30 ml of dimethylformamide was heated at 85° C. for three days. The reaction mixture was cooled to ambient temperature and washed with 6×20 ml portions of water, dried, and concentrated to give 1.4g (63.6%) of product, which was purified by dissolving in carbon tetrachloride and passing through a small basic alumina column, $n_D^{23.5} = 1.4631$.

| Elemental Analysis: | C | H | N |
| --- | --- | --- | --- |
| Calculated for $C_7H_{12}F_4N_8$: | 29.58 | 4.23 | 39.44 |
| Found: | 29.76 | 4.27 | 39.16 |

EXAMPLE V

Preparation of bis (1,3-Diazido-2-propyl) Oxalate

A mixture of 8.4g (0.06 mole) of 1,3-diazido-2-propanol, 3.8g (0.03 mole) of oxalyl chloride, 1.2g of anhydrous aluminum chloride, and 45 ml of ethylene dichloride was refluxed for 60 hours. The reaction mixture was cooled, washed with dilute hydrochloric acid, dilute sodium bicarbonate solution, water, dried, and concentrated to give 7g (70%) of liquid product, $n_D^{24.5} = 1.5140$. Purification of the product in carbon tetrachloride over a basic alumina column gave a solid, m.p. 54°-55° C.

| Elemental Analysis: | C | H | N |
| --- | --- | --- | --- |
| Calculated for $C_8H_{10}N_{12}O_4$: | 28.40 | 2.96 | 49.70 |
| Found: | 27.82 | 2.97 | 48.70 |

EXAMPLE VI

Preparation of 1,3-Diazido-2-propyl 4,4,4-Trinitrobutyrate

A solution of 25g (0.1 mole) of 4,4,4-trinitrobutyryl chloride, 14.7g (0.1 mole) of 1,3-diazido-2-propanol, and 50 ml of ethylene dichloride was refluxed for one week. The solution was cooled, washed with water, dried, and concentrated to give 25.5g (73.5%) of amber liquid. The product was purified by dissolving in carbon tetrachloride and passing through a neutral alumina column. Concentration of this solution gave a yellow liquid, $n_D^{24} = 1.5029$, $d^{25} = 1.464$. The infrared spectrum showed the expected strong absorption for azide (4.7μ), carbonyl (5.8μ), and nitro (6.2μ).

| Elemental Analysis: | C | H | N |
| --- | --- | --- | --- |
| Calculated for $C_7H_9N_9O_8$: | 24.21 | 2.59 | 36.31 |
| Found: | 23.61 | 2.76 | 35.38 |

EXAMPLE VII

Preparation of 1,3-Diazido-2-propyl 4,4,4-Fluorodinitrobutyrate

A solution of 6.4g (0.03 mole) of 4,4,4-fluorodinitrobuyryl chloride, 4.3g (0.03 mole) of 1,3-diazido-2-propanol, and 25 ml of ethylene dichloride was refluxed for 40 hours. The solution was cooled, washed with water, dried, and concentrated to give 8.0g (83.3%) of light-yellow liquid. The product was purified by dissolving in carbon tetrachloride and passing through a neutral alumina column. Concentrations of this solution gave a colorless liquid, $n_D^{23.5} = 1.4875$, $d^{25} = 1.435$.

The infrared spectrum showed the expected strong absorption for azide (4.7μ), carbonyl (5.8μ) and nitro (6.2μ).

| Elemental Analysis: | C | H | N |
| --- | --- | --- | --- |
| Calculated for $C_7H_9FN_8O_6$: | 26.25 | 2.81 | 35.00 |
| Found: | 27.01 | 3.10 | 34.45 |

EXAMPLE VIII

N-(Trinitroethyl)-N-(3-Azidopropyl)Nitramine (TAPNA)

To a solution of 13.8g (0.1 mole) of 3-azidopropyl amine hydrochloride, 21.7g (0.12 mole) of trinitroethanol, and 60 ml of water was added dropwise a solution of 4.0g (0.1 mole) of sodium hydroxide in 30 ml of water. The oil, which separated, was extracted with methylene chloride, washed with water, and dried.

The methylene chloride solution of N-(trinitroethyl)-N-(3-azidopropyl) amine was added to a solution of 50 ml of acetic anhydride and 25 ml of 99% nitric acid at 5°-10° C. The reaction mixture was allowed to warm to ambient temperature with stirring. The methylene chloride layer was separated, washed with water, dried, and concentrated to give 8.2g (26.6%) of amber oil. The product was purified by elutriating with carbon tetrachloride/methylene chloride solution from a neutral alumina column to give a light-yellow liquid $d^{25} = 1.5195$, $n_D^{26} = 1.5120$.

| Elemental Analysis: | C | H | N |
| --- | --- | --- | --- |
| Calculated for $C_5H_8N_8O_8$: | 19.48 | 2.60 | 36.36 |
| Found: | 19.52 | 2.80 | 35.39 |

It has been found that azido compounds, such as those described above, have physical properties which are highly desirable for propellant and explosive formulations. Thus, for example, the compound of Example I, above, has an impact sensitivity above 60 inch pounds and an initial exotherm of 195° C. The compound of Example VII, above, has an impact sensitivity greater than 150 inch pounds and an initial exotherm of 188° C.

A family of propellant compositions were formulated, employing conventional ingredients with the azido compounds. It was found that the use of the azido compounds substantially increased the burn rate of these propellant compositions and that the azido compounds lend themselves to "tailoring" of the propellant formulations to enhance desired properties. The specific details of the propellant formulations and the characteristics thereof are available, but have been omitted from this specification to avoid the necessity of security classification.

Obviously, numerous variations and modifications can be made without departing from the present invention. Accordingly, it should be understood that the forms of the invention described above are illustrative only and are not intended to limit the scope of the present invention.

We claim:

1. An organic aliphatic ether compound containing both fluorodinitro and azido moieties having the structure of $FC(NO_2)_2$—$CH_2$—$O$—$CH_2$—$R_1$ wherein $R_1$ is —$CH_2N_3$ and —$O$—$CH$—$(CH_2N_3)_2$.

2. An organic nitramine compound containing both trinitromethyl and azido moieties having the structure of

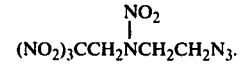

3. An organic alkane compound containing both gemdifluoroamine and azido moieties having the structure of

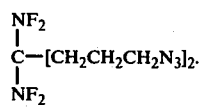

* * * * *